United States Patent
Fox et al.

(10) Patent No.: US 10,783,222 B2
(45) Date of Patent: Sep. 22, 2020

(54) CONVERTING UNORGANIZED MEDICAL DATA FOR VIEWING

(71) Applicant: Covidien LP, Mansfield, MA (US)

(72) Inventors: David Anthony Fox, Longmont, CO (US); Robert T. Boyer, Longmont, CO (US)

(73) Assignee: Covidien LLP, Mansfield, MA (US)

( * ) Notice: Subject to any disclaimer, the term of this patent is extended or adjusted under 35 U.S.C. 154(b) by 1276 days.

(21) Appl. No.: 15/007,408

(22) Filed: Jan. 27, 2016

(65) Prior Publication Data
US 2017/0213004 A1 Jul. 27, 2017

(51) Int. Cl.
*G06Q 10/00* (2012.01)
*G06F 19/00* (2018.01)

(52) U.S. Cl.
CPC ................. *G06F 19/3418* (2013.01)

(58) Field of Classification Search
USPC ........................................ 705/2–3
See application file for complete search history.

(56) References Cited

U.S. PATENT DOCUMENTS

| | | | | |
|---|---|---|---|---|
| 7,430,608 B2 * | 9/2008 | Noonan | ............... | G06F 19/3418 709/230 |
| 8,126,732 B2 * | 2/2012 | Dicks | ..................... | G06Q 50/24 705/2 |
| 8,868,436 B2 * | 10/2014 | Gotthardt | ............ | G06F 21/6245 705/2 |
| 2005/0192838 A1 * | 9/2005 | Jones | .................... | G06F 19/324 705/2 |
| 2007/0255348 A1 * | 11/2007 | Holtzclaw | ............ | A61B 5/0002 607/60 |
| 2011/0166880 A1 * | 7/2011 | Keynan | .................. | G06Q 10/10 705/2 |
| 2011/0184752 A1 * | 7/2011 | Ray | ........................ | G16H 15/00 705/2 |
| 2013/0211854 A1 * | 8/2013 | Wagstaff | ................ | G06Q 50/22 705/2 |
| 2014/0002234 A1 * | 1/2014 | Alwan | .................. | G16H 10/60 340/5.1 |

OTHER PUBLICATIONS

Torres-Rios, Emmanuel, et al. "A method to determine the gate bias-dependent and gate bias-independent components of MOSFET series resistance from S-parameters." IEEE transactions on electron devices 53.3 (2006): 571-573.*

* cited by examiner

*Primary Examiner* — Mark Holcomb

(57) ABSTRACT

Methods, systems, and devices for wireless patient monitoring and medical sensing are described. The methods, systems, and devices may include functionality for receiving a medical dataset associated with a patient, the medical dataset including a plurality of physiological measurements taken from the patient and a plurality of parameters associated with the plurality of physiological measurements. The methods, systems, and devices may also identify one or more groups of parameters from the plurality of parameters within the medical dataset, determine at least a medical device type from which at least a portion of the plurality of physiological measurements were measured, the determining based at least in part on the one or more identified groups of parameters; and display at least a subset of the plurality of physiological measurements from the medical dataset.

14 Claims, 13 Drawing Sheets

```
MSH|^~\&|GATEWAY_CAPSULE^0054674000000001^EUI64|GATEWAY_CAPSULE^0054674000000001^EUI64|NIS
TManager_ADMIN|NIST|20151210145031.328+0000||ORU^R01|5c10145031390a3|P|2.6|||NE|AL|||88591|IHE_PCD_
ORU_R01^IHE PCD^1.3.6.1.4.1.19376.1.6.1.1.1^ISO|
PID||||PatientID|
PV1||||ICU^RoomNum^BedNum|
OBR|||CAPSULE_VITALSYNC^GATEWAY_CAPSULE^0054674000000001^EUI64|CAPSULE_VITALSYNC^GATEW
AY_CAPSULE^0054674000000001^EUI64|99999^MDC_DEV_GATEWAY^MDC|||DATETIME|DATETIME||ICU^Room
Num^BedNum|||Capnography^CapsuleTechnologie^Capnostream20^{F6121D17-A2B2-4B64-8891-E76BC92B8A85}|
OBX|1|NM|PulseRateHighViolation^Pulse Rate High Violation|1.3.1.2.3|0.000000|^unitless|||||F|||DATETIME|
OBX|2|NM|PulseRateLowViolation^Pulse Rate Low Violation|1.3.1.2.4|0.000000|^unitless|||||F|||DATETIME|
OBX|3|NM|PulseRate^Pulse Rate|1.3.1.2|60.000000|^bpm|||||F|||DATETIME|
OBX|4|NM|PulseRateLimitHigh^Pulse Rate Limit High|1.3.1.2.1|150.000000|^bpm|||||F|||DATETIME|
OBX|5|NM|PulseRateLimitLow^Pulse Rate Limit Low|1.3.1.2.2|50.000000|^bpm|||||F|||DATETIME|
OBX|6|NM|ApneaInterval^Apnea Interval|1.42.0.91|9.000000|^s|||||F||SETTING|DATETIME|
OBX|7|NM|SpO2HighViolation^SpO2 High Violation|1.3.1.1.3|1.000000|^unitless|||||F|||DATETIME|
OBX|8|NM|SpO2LowViolation^SpO2 Low Violation|1.3.1.1.4|0.000000|^unitless|||||F|||DATETIME|
OBX|9|NM|EtCO2^EtCO2|1.11.1.1|36.000000|^mmHg|||||F|||DATETIME|
OBX|10|NM|EtCO2LimitHigh^EtCO2 UAL|1.11.1.1.1|17.000000|^mmHg|||||F|||DATETIME|
OBX|11|NM|EtCO2LimitLow^EtCO2 LAL|1.11.1.1.2|5.000000|^mmHg|||||F|||DATETIME|
OBX|12|NM|FiCO2^FiCO2|1.11.1.3|37.000000|^mmHg|||||F|||DATETIME|
OBX|13|NM|FiCO2LimitHigh^FiCO2 Limit High|1.11.1.1.3.1|56.000000|^mmHg|||||F|||DATETIME|
OBX|14|NM|RespirationRate^Respiration Rate|1.11.3.1|38.000000|^brpm|||||F|||DATETIME|
OBX|15|NM|RespRateLimitHigh^Respiration Rate Limit High|1.11.3.1.1.2|15.000000|^brpm|||||F|||DATETIME|
OBX|16|NM|RespRateLimitLow^Respiration Rate Limit Low|1.11.3.1.2|4.000000|^brpm|||||F|||DATETIME|
OBX|17|NM|SpO2^SpO2|1.3.1.1|39.000000|^pcnt|||||F|||DATETIME|
OBX|18|NM|SpO2LimitHigh^SpO2 limit High|1.3.1.1.1|99.000000|^pcnt|||||F|||DATETIME|
OBX|19|NM|SpO2LimitLow^SpO2 limit Low|1.3.1.1.2|95.000000|^pcnt|||||F|||DATETIME|
```

CONVERTING UNORGANIZED MEDICAL DATA FOR VIEWING

BACKGROUND

The following relates generally to patient monitoring systems and medical sensors, and more specifically to visualizing medical data by converting unorganized medical data for viewing.

In a medical care facility such as a hospital, a patient may be monitored by medical devices or systems that measure parameters (e.g., physiological parameters such as heart rate, respiratory rate, blood pressure, etc.) of the patient. Other parameters associated with the patient (e.g., location information, patient identification information, etc.) may also be obtained using various other medical devices or by a clinician monitoring the patient.

As the patient is monitored, data from medical devices (e.g., measurements obtained from medical devices) and data recorded by clinicians monitoring the patient (e.g., measurements from manually performed tests, patient condition information, etc.) may be collected over time. In some cases, the collected data may be arranged in a particular format that is not an efficient or logical format when being viewed by a clinician. For example, the collected data may be arranged in format that optimizes the space allocated for storage of the data. Accordingly, when a clinician attempts to review data arranged in such a format, it may be difficult to quickly and efficiently identify data that is relevant or beneficial to the clinician at the time of reviewing. For example, if data from multiple devices or clinicians are arranged without separation, distinguishing between data measured by different devices may be challenging. In some cases, identifying relevant information may not even be possible without knowledge of how the data is arranged (e.g., if data are arranged as a list of encoded numbers). However, knowledge of how the data is arranged may not always be available to the clinician reviewing the data. Thus belated diagnosis or misdiagnosis of a patient may occur as a result of the unorganized data.

SUMMARY

The described features generally relate to methods and devices for visualizing medical data as medical data associated with a patient may be collected and arranged in a format that is unsuitable for viewing by a clinician. To more efficiently present medical data for viewing, measurements, parameters, or groups of parameters of an unorganized medical dataset may be identified and analysis of the identified measurements, parameters, or groups of parameters may be performed to determine the type of medical device associated with the identified measurements, parameters, or groups of parameters. The determination may involve comparing medical data to parameters associated with one or more medical devices. A particular medical device may then be determined based on the comparison and at least a subset of the data in the unorganized medical dataset may be displayed in a format that is more suitable for viewing by a clinician.

In certain scenarios, the collected data may be stored on a database or server and may be accessible or accessed by a clinician at a later time. In other situations, data associated with a patient may be streamed from a medical device to a local or mobile device to be viewed by a clinician. When the data is streamed in a format unsuitable for viewing, the medical device streaming the data may be determined and at least a subset of the streaming data may be displayed on a local or mobile device in a format that is more suitable for viewing by a clinician.

For example, data may be displayed in a visual format corresponding to a visual format of the medical device that obtained or is obtaining the data.

Embodiments of systems and devices for visualizing medical data are also described. In accordance with certain aspects, a system includes a memory configured to receive and store a medical dataset, an identification unit configured to identify measurements, parameters, or one or more groups of parameters from the medical dataset, a determination unit configured to determine a medical device associated with the one or more of the identified measurements, parameters, or one or more groups of parameters, and a display unit configured to display a portion of the medical dataset based on the determination.

Certain embodiments of the present disclosure may include some, all, or none of the above advantages or features. One or more other technical advantages or features may be readily apparent to those skilled in the art from the figures, descriptions, and claims included herein. Moreover, while specific advantages or features have been enumerated above, various embodiments may include all, some, or none of the enumerated advantages or features.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

FIG. 6A shows an example medical dataset in accordance with aspects of the present disclosure;

DETAILED DESCRIPTION

In accordance with various embodiments described herein, medical data may be visualized by converting disorganized data from a medical dataset associated with a patient into a format more suitable for viewing by a clinician. The data may be associated with a patient that was or is being monitored in a health care facility such as a hospital. The data may be obtained from medical devices attached, connected, or otherwise associated with the patient or from a clinician performing one or more tests on the patient. For example, a clinician responsible for the patient may record observations regarding patient condition, perform tests and manually obtain measurements associated with the patient, identify patient, device, or facility specific information, or record any other information associated with the patient.

In some cases, the data may be transmitted (e.g., from a medical device to a mobile device) or stored (e.g., in a database) in a format unsuitable for viewing by a clinician. However, by analyzing the data in accordance with aspects of the present disclosure, a medical device associated with at least a portion of the data may be determined and at least a subset of the data may be displayed in a more suitable format for viewing based on the determination.

To determine the medical device associated with at least a subset of the dataset, parameters or one or more groups of parameters within the dataset may be identified and compared to parameters or one or more groups of parameters associated with or indicative of one or more medical devices. Based on the comparison, a medical device associated with at least a subset of the dataset may be determined and data from the dataset may be displayed, viewed, or otherwise presented based on the determined medical device. In some embodiments, the dataset may be displayed based on a manufacturer, model, or type associated with a medical device or may be based at least in part on clinician preference, health care facility information, or patient condition, among others.

Figure 1:
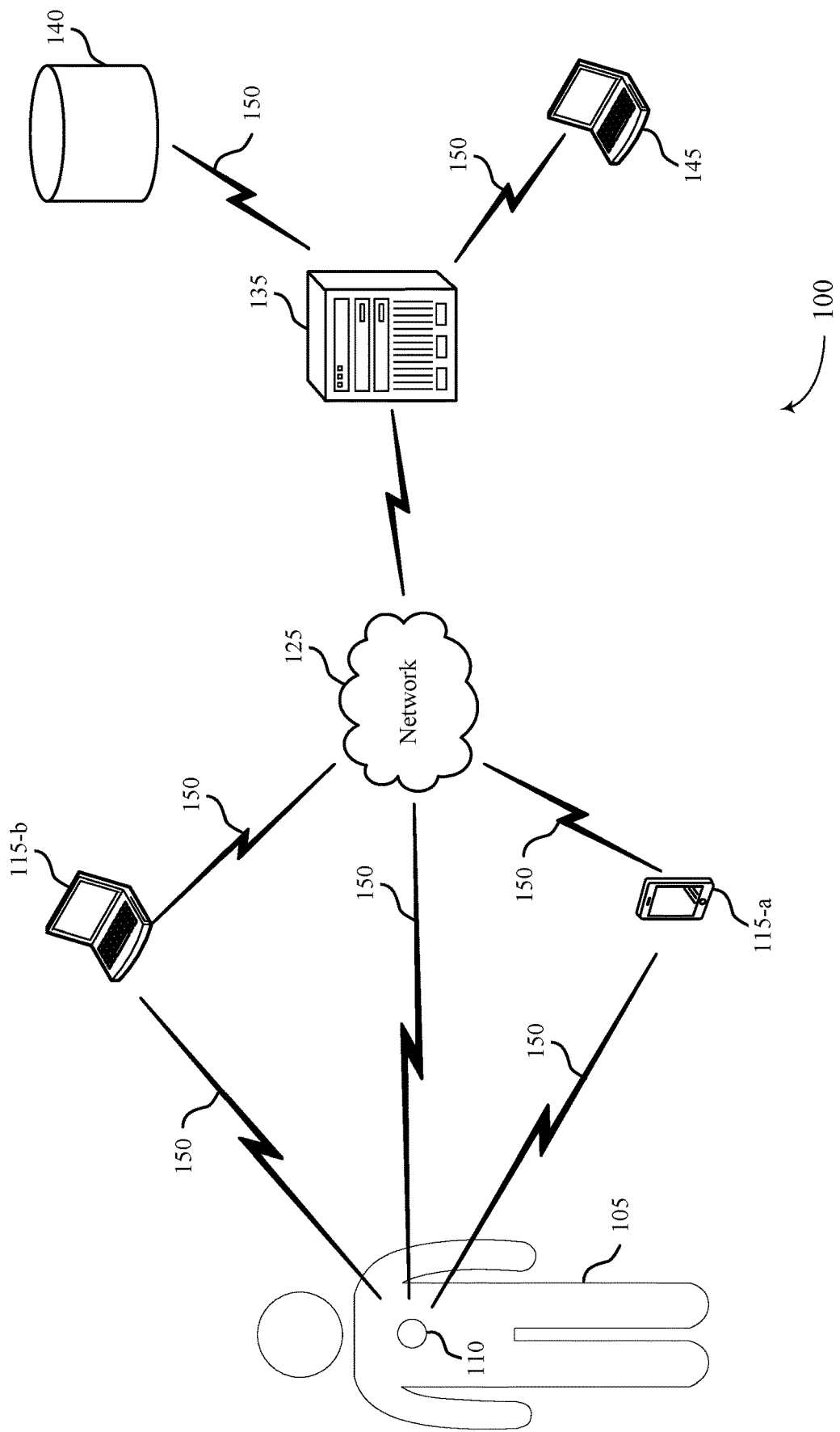
FIG. 1 illustrates an example of a wireless sensor system that supports visualizing medical data in accordance with aspects of the present disclosure.

FIG. 1 illustrates an example of a wireless patient monitoring system 100 in accordance with various embodiments of the present disclosure. The wireless patient monitoring system 100 includes a patient 105 wearing, carrying, disposed on, or otherwise coupled with a medical device 110. Although a single medical device 110 is shown, multiple medical devices 110 may be associated with the patient 105. The patient 105 may be a patient in a hospital, nursing home, home care, or other medical care facility. The medical device 110 may transmit signals via communications links 150 to computing devices 115 or to a network 125. The communication links 150 may be wired or wireless communication links. In some cases, the medical device 110 may be used in conjunction with another medical device 110 to observe, record, collect, or otherwise obtain data associated with the patient. Data may also be obtained by a clinician responsible for monitoring the patient. For example, a blood pressure test may be performed by a nurse responsible for the patient and any measurements from the blood pressure test or observations associated with the patient may be recorded by the nurse.

Computing device 115-a may be a wireless device such as a tablet, cellular phone, personal digital assistant (PDA), dedicated receiver or other similar device or a spatially distributed network of devices configured to receive signals from the medical device 110.

Computing device 115-b may be a wireless laptop computer or mobile computer station configured to receive signals from the medical device 110. The computing devices 115 may be in communication with a central station 135 via network 125. In accordance with various embodiments, computing devices 115 may be configured to obtain data associated with the patient 105.

In some embodiments, the data obtained may include physiological measurements (e.g., heart rate, respiratory rate, blood pressure, oxygen saturation, etc.) of the patient 105. Data may be obtained by the medical device 110 continuously, periodically, intermittently, or at the request of a clinician or other medical device 110. In some cases, a single medical device 110 may be configured to obtain multiple physiological parameters associated with the patient or other data (e.g., location data of the patient, health care facility information). Further, the medical device 110 may also be used by a clinician to manually obtain data associated with the patient 105. For example, a clinician may use one or more medical devices 110 to obtain measurements of patient blood pressure and the measurements may then be recorded or input (e.g., by the clinician) to a dataset associated with the patient 105.

In some embodiments, the medical device 110 may also communicate directly with the central station 135 via the network 125. The central station 135 may be a server or a clinician station located within a health care facility or in a remote location. The central station 135 may be in further communication with one or more remote computing devices 145, thus allowing a clinician to remotely monitor the patient 105. The central station 135 may also be in communication with various databases 140 where collected data may be stored.

The medical device 110 may include one or more sensors configured to collect a variety of parameters (e.g., physiological parameters) as well as other data related to the patient 105 (e.g., location, activity level, and movement of the patient 105). For example, the medical device 110 may include a pulse oximetry (SpO2) sensor, a heart rate sensor, a blood pressure sensor, a pressure sensor, an electrocardiogram (ECG) sensor, a respiratory rate sensor, a glucose level sensor, a body temperature sensor, an accelerometer, a global positioning sensor, a sensor which triangulates position from multiple computing devices 115, and any other sensor configured to collect physiological, patient, facility, location, or motion data. As discussed herein, the obtained data may include any information related to the patient 105 and may be stored or recorded as a set of data (i.e., a dataset) and in some cases, the dataset may be arranged in a format unsuitable for viewing by a clinician (e.g., the data obtained may be arranged as an encoded series of numbers readable by a computer such as computing devices 115 or central station 135).

The medical device 110 may be coupled with the patient 105 in a variety of ways. For example, the medical device 110 may be directly coupled with the patient 105 (e.g., physically connected to the patient's chest, worn around the patient's wrist, or attached to the patient's finger). The medical device 110 may be indirectly coupled with the patient 105 so that movement of the patient 105 is detected even though the sensor is not in direct contact with, or physically connected to, the patient 105. The data obtained by the medical device 110 may be conveyed (e.g., wired or wirelessly) to one or more of the computing devices 115 or to the remote computing device 145 (via the network 125 or central station 135). Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.).

In accordance with various embodiments, methods and systems are described for visualizing data associated with patient 105 obtained by one or more medical devices 110 or by a clinician responsible for the patient 105. As described in detail below, data associated with the patient 105 may be recorded in a dataset and arranged in a format unsuitable for viewing by a clinician. Using data within the dataset (e.g., measurements, parameters, or one or more groups of parameters), a disorganized dataset may be converted and presented in a format more suitable for viewing by a clinician. In some embodiments, data may be received at a computing device 115, or a remote computing device 145 from the medical device 110 or may be obtained at the medical device 110 using one or more sensors. One or more medical devices 110 associated with or indicative of the obtained data may be determined based on measurements, parameters, or one or more groups of parameters within the dataset and at least a subset of the data within the medical dataset may be presented for viewing. In accordance with various embodiments, data may be presented on a display unit that may be associated with one or more of computing devices 115 or remote computing devices 145. Data may be displayed in a format that is more suitable for viewing by a clinician. For instance, measurements, parameters or one or more groups of parameters within the disorganized dataset associated with a particular medical device may be displayed in a format associated with the particular device type, device manufacturer, or device model (i.e., similar to how data is typically displayed on that particular medical device).

Figure 2A:
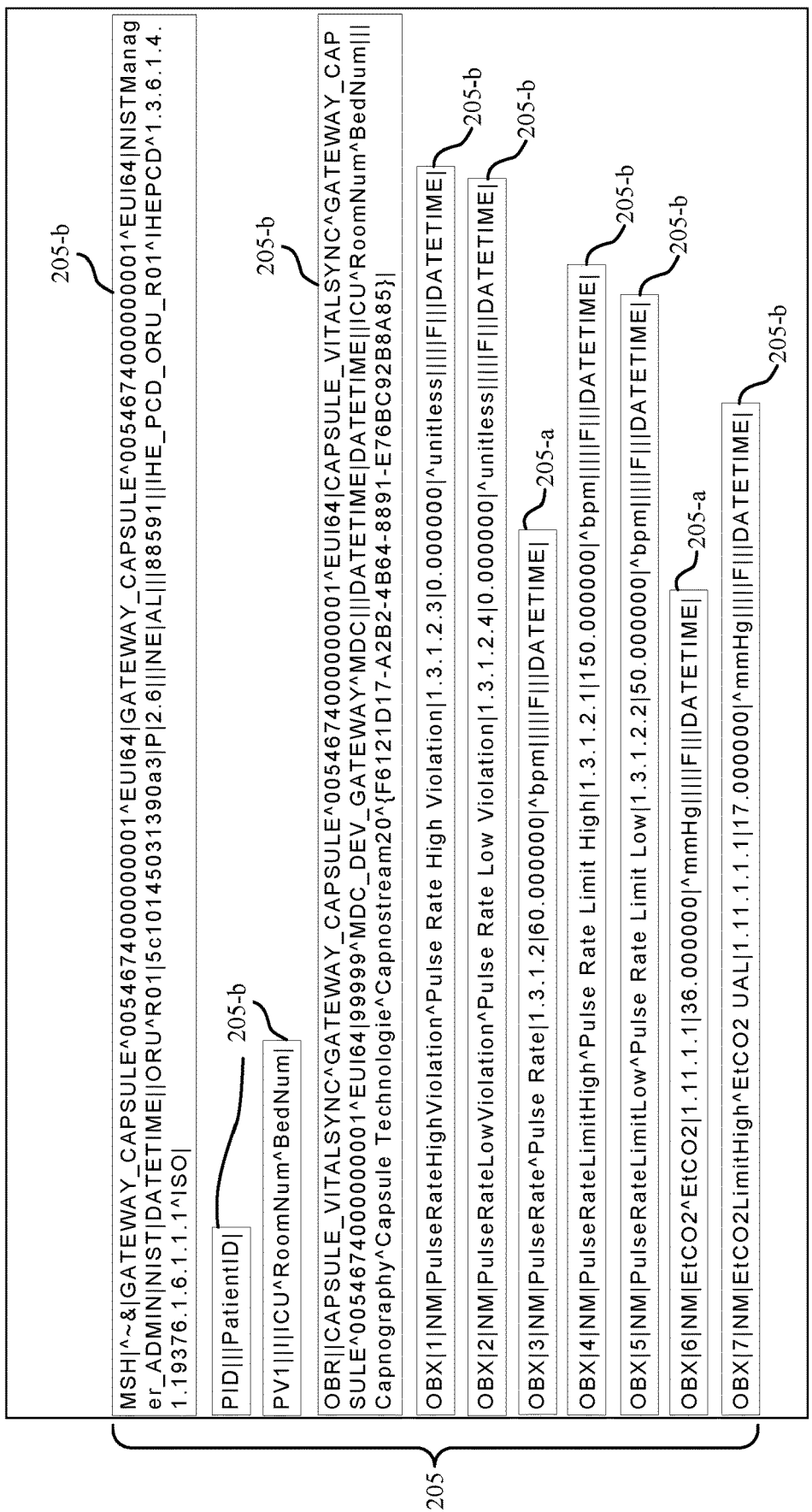
FIGS. 2A and 2B illustrate examples of a medical dataset in accordance with aspects of the present disclosure.
Figure 2B:
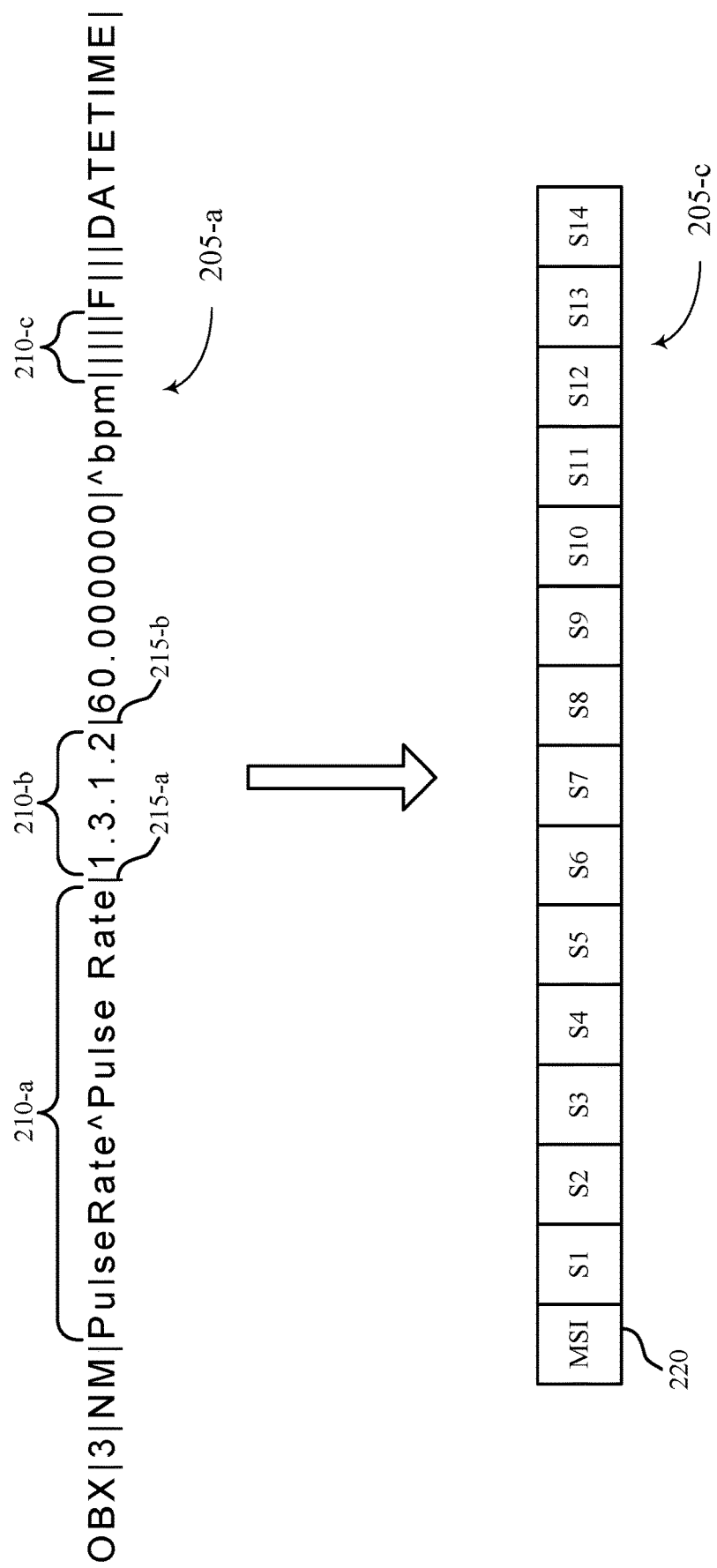

FIGS. 2A-2B illustrate examples of a dataset 200 containing data associated with a patient 105 in accordance with various aspects of the present disclosure. The dataset 200 may represent a complete dataset of the patient 105 or may represent only a portion of an entire dataset of the patient 105. In this example, the dataset 200 is a Health Level 7 (HL7, an international standards organization for health information) dataset and therefore includes data arranged in a standard HL7 format. Although the dataset 200 is arranged in HL7 format, it should be understood that dataset 200 is for purposes of illustration only and other types of datasets, formats, and arrangements of data may be considered without departing from the scope of the present disclosure. For example, in some embodiments, the dataset 200 may be a Fast Healthcare Interoperability Resources (FHIR) dataset, a Clinical Document Architecture (CDA) dataset, a Consolidated CDA (C-CDA) dataset, or any other dataset related to electronic health records or personal health records.

In FIG. 2A, dataset 200 (also referred to as an HL7 message) includes multiple message segments 205, each of which includes data (e.g., measurements, parameters, groups of parameters, etc.) of the patient 105 or associated with the message segments 205. As shown, message segments 205-*a* include data related to measurements of one or more physiological parameters of the patient 105, while message segments 205-*b* include data related to information other than measurements of one or more physiological parameters of the patient 105, as discussed further below with respect to FIG. 2B. In some examples, the dataset 200 may include information related to a facility associated with the dataset 200 (e.g., a hospital from which the dataset 200 is streaming or a data storage facility at which the dataset 200 is or was stored). As such, although not shown in FIG. 2A, information other than information associated with the patient 105 may be included in the dataset 200.

Data of the dataset 200 may be obtained using one or more medical devices 110 or recorded by a clinician as described above with reference to FIG. 1. Further, data of the dataset 200 may be transmitted from one or more medical devices 110 to computing devices 115, central station 135, or remote computing devices 145 (e.g., via network 125) or may be stored (e.g., on various databases 140) as also described above.

Referring now to FIG. 2B, a message segment 205-*a* of dataset 200 is shown. Message segment 205-*a* includes a plurality of parameters 210 which may be associated with the patient 105 (in this case, the plurality of parameters 210 relate to a physiological measurement of the patient 105). As shown, each of the plurality of parameters 210 are separated from one another by separators 215. For example, parameter 210-*a* is separated from parameter 210-*b* by separator 215-*a*.

The format in which the message segment 205-*a* is arranged may depend on a standard format associated with the entire dataset 200 or may be based on a medical device that corresponds to the message segment 205-*a* (e.g., the format of the medical device that generated message segment 205-*a*). In the example message segment 205-*a*, the format of the message segment 205-*a* is represented by message segment format 205-*c* and includes a message segment identifier (MSI) 220 followed by fourteen sequences S1 through S14. Although fourteen sequences are shown, the number of sequences may be different in each message segment 205 of the dataset 200 and may be based at least in part on the MSI 220, the format of the dataset 200, or other factors such as a health care facility or medical device associated with the message segment 205-*a*. Each of the sequences S1-S14 may contain data used to identify information related to the message segment 205 or identify data associated with the patient 105.

For example, using a standard HL7 format, message 205-*a* is an observation message segment having an Observation/Result (OBX) MSI 220. Sequence 1 (S1) represents the OBX message segment index number (for message segment 205-*a*, S1 is 3). While message segment 205-*a* is not the third message segment in dataset 200, the message segment 205-*a* is the third OBX message segment of the dataset 200. In addition, Sequence 3 (S3) identifies the physiological parameter being measured, which is Pulse Rate (PulseRate^PulseRate, parameter 210-*a*) for message segment 205-*a*. Further, S5 and S6 represent the value and corresponding units, respectively, for the physiological parameter being measured. Thus, for message segment 205-*a*, the measured pulse rate is 60 beats per minute (bpm). Other information related to the message segment 205-*a* may also be included in sequences S1 through S14. For instance, the date and time at which the physiological parameter was measured or the observation was taken is indicated at Sequence 14 (S14). In addition, some sequences in a message segment 205 may not include any information, as represented by null parameters 210-*c* of message segment 205-*a*. As should be understood, sequences (e.g., S1 through S14) refer to the format of a message segment 205 in a dataset 200, while parameters 210 of the message segment 205 indicate data associated with the patient 105 or other information related to the message segment 205.

Referring again to FIG. 2A, a dataset 200 may include multiple message segments 205 having different MSIs 220 (e.g., PID, PV1, OBR, OBX, etc.). While there may be relevant data contained with dataset 200, it may be difficult for a clinician to review dataset 200 as presented in FIG. 2A. In addition, in some cases, separators 215 may not be included in one or more message segments 205 making interpretation of dataset 200 by a clinician even more difficult. As such, in accordance with one or more embodiments, data within dataset 200 may be analyzed and data relevant to a clinician may be presented in a format more suitable for viewing.

Figure 3A:
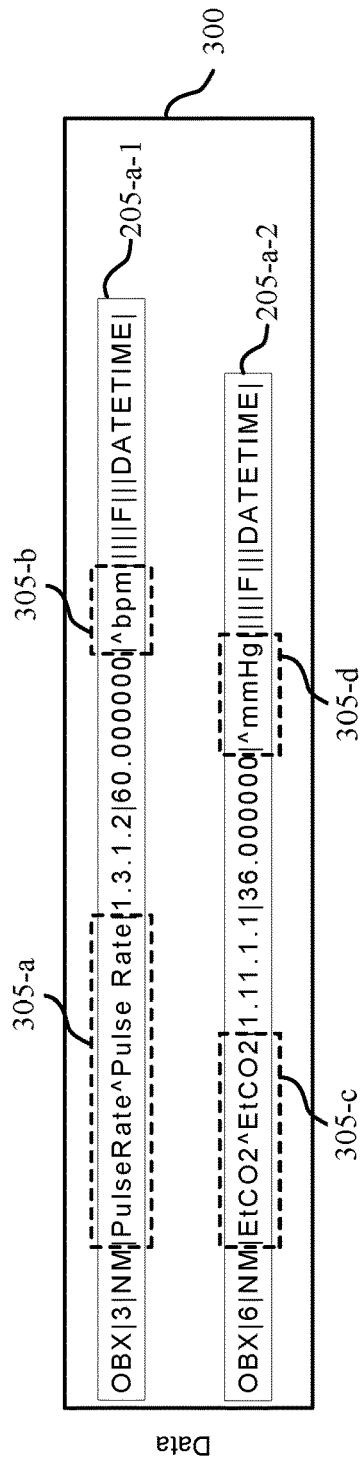
FIGS. 3A-3B illustrate examples of message segment groups in accordance with aspects of the present disclosure.

FIG. 3A shows a message segment group 300 including message segments 205-*a*-1 and 205-*a*-2, which may be an example of aspects of dataset 200 described with reference to FIGS. 2A-2B. As shown in FIG. 3A, message segments 205-*a*-1 and 205-*a*-2 of message segment group 300 include parameters related to physiological measurements taken from the patient as well as other parameters (e.g., parameters associated with the physiological measurements or the message segment itself). In this example, message segment 205-*a*-1 includes a pulse rate parameter 305-*a* and units (bpm) associated with measuring pulse rate, as indicated by parameter 305-*b* (based on Sequences 3 and 6 of message segment 205-*a*-1). Message segment 205-*a*-2 includes a carbon dioxide concentration (EtCO2) parameter 305-*c* and units (mmHg) associated with measuring carbon dioxide concentration, as indicated by parameter 305-*d* (based on Sequences 3 and 6 of message segment 205-*a*-2).

As shown by message segment group 300, a parameter type (i.e., Pulse Rate, EtCO2) and associated units (i.e., bpm, mmHg) are included in message segments 205-*a*-1 and 205-*a*-2. The parameter type, order of parameters, or number of parameters may vary by device type, device model, or device manufacturer. In some embodiments, information related to the parameter type, order of parameters, or number of parameters of different devices may be predetermined or stored in a memory of a medical device 110, computing device 115, a central station 135, or a remote computing device 145, or may be stored on various databases 140 as described with reference to FIG. 1. Therefore, by comparing the parameters in message segments 205-*a*-1 and 205-*a*-2 with parameters known to correspond with or are indicative of one or more devices, a device associated with the message segment group 300 may be determined. In other words, in accordance with various embodiments described herein, the device (i.e., device type, device model, or device manufacturer) that originally output the message segment group 300 (and the associated physiological measurements) may be determined from the unorganized dataset 200 by matching parameters of the message segment group 300 (e.g., parameter type, order of parameters, or number of parameters that are listed) to a parameter grouping or format that is known to be output by a particular device (e.g., device type, device model, or device manufacturer).

Figure 3B:
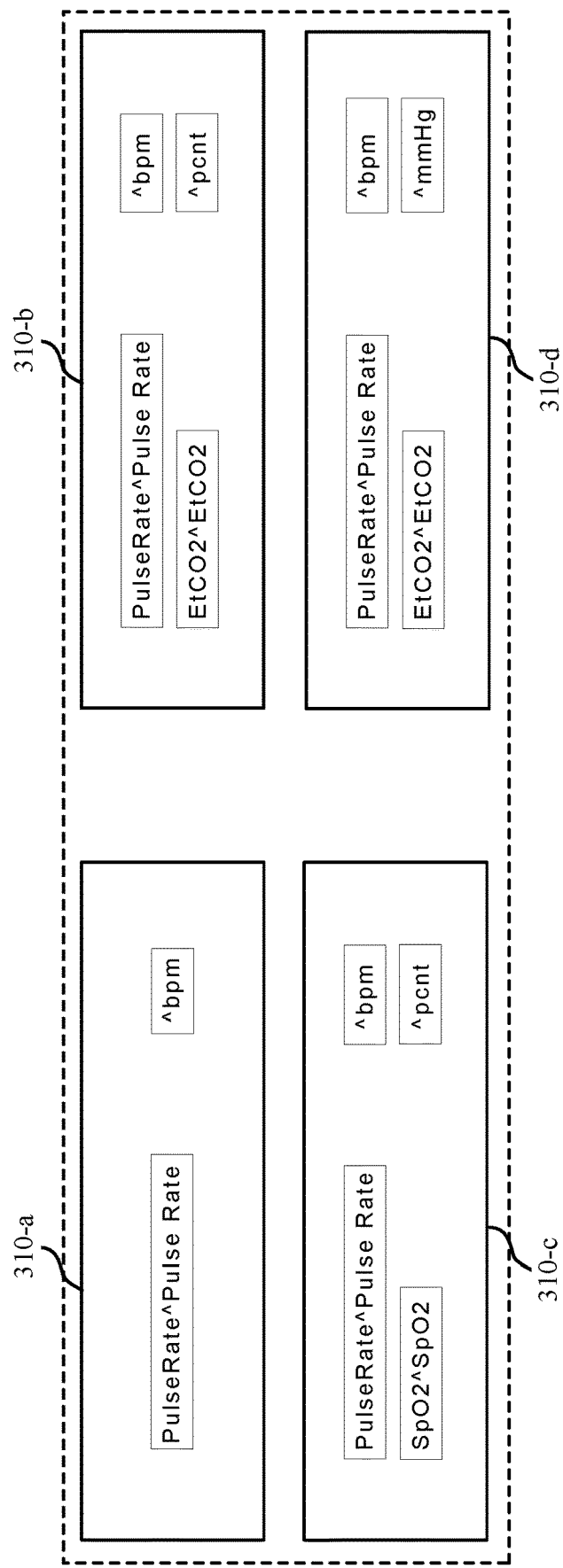

For example, as shown in FIG. 3B, parameter groups 310 of four different devices may be predetermined or stored in a memory of a medical device 110, computing device 115, a central station 135, or a remote computing device 145, or may be stored on various databases 140 as described with reference to FIG. 1. Parameter group 310-*a* may be known to correspond with a first device that measures and outputs pulse rate in bpm. Parameter group 310-*b* may be known to correspond with a second device that measures and outputs pulse rate in bpm and also measures an outputs EtCO2 as a percentage. Parameter group 310-*c* may be known to correspond with a third device that measures and outputs pulse rate in bpm and also measures and outputs oxygen saturation (SpO2) as a percentage. Parameter group 310-*d* may be known to correspond with a fourth device that measures and outputs pulse rate in bpm and also measures and outputs carbon dioxide concentration in mmHg. In this instance, as the parameters 305-*a*, 305-*b*, 305-*c*, and 305-*d* match with the parameters group 310-*d* known to correspond with the fourth device, it may be determined that the fourth device generated, recorded, or otherwise obtained the message segments 300. Once the device that originally output message segments 205-*a*-1 and 205-*a*-2 is determined, at least a portion of the message segment group 300, or other information within dataset 200 may be output on a display, such as the display shown in FIG. 6B as will be discussed below.

Figure 4A:
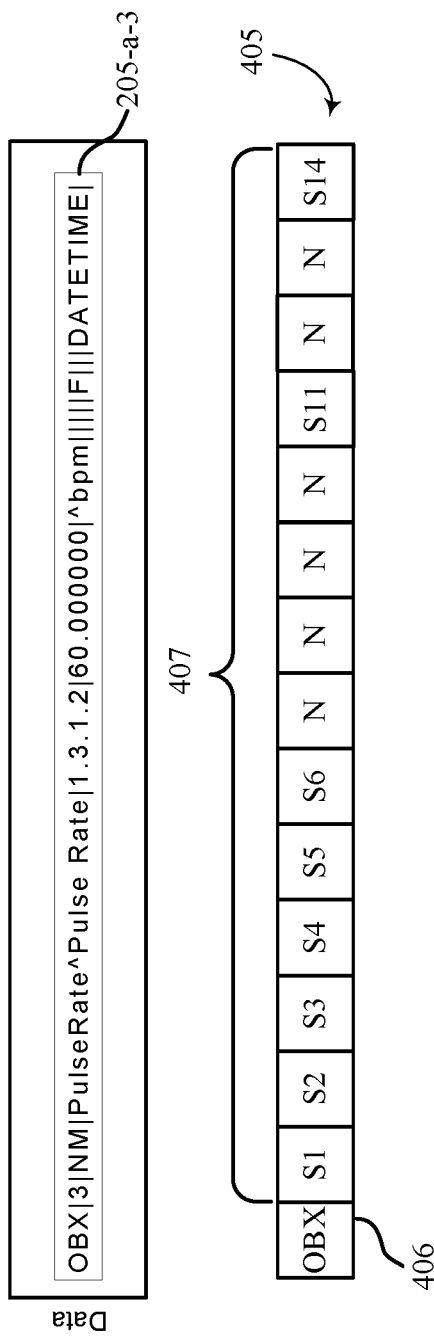
FIGS. 4A-4B illustrate examples of message segment formats in accordance with aspects of the present disclosure.

FIG. 4A shows a message segment 205-*a*-3 from dataset 200. In FIG. 4A, message segment 205-*a*-3 includes parameters related to a physiological measurement taken from the patient as well as other parameters associated with the physiological measurement or message segment 205-*a*-3. For example, as shown in message segment 205-*a*-3, a pulse rate of 60 bpm (based on Sequences 3, 5, and 6) is measured at a given date and time (based on Sequence 14). In one or more embodiments, the message segment format 405 of message segment 205-*a*-3 may be used to determine a device (i.e., a device type, a device model, or a device manufacturer) associated with the message segment 205-*a*-3.

As describe herein, the message segment format relates to the arrangement of the message segment and may refer to the order of parameters in the message segment, the number of parameters or null values in a message segment, the number of sequences in a message segment, the MSI of a message segment, or the like. The message segment format may vary by device type, device model, or device manufacturer. In some embodiments, information related to the message segment format corresponding to different devices may be predetermined or stored in a memory of a medical device 110, computing device 115, a central station 135, or a remote computing device 145, or may be stored on various databases 140 as described with reference to FIG. 1. Therefore, by comparing the message segment format 405 of message segment 205-*a*-3 with message segment formats 410 known to correspond with or are indicative of one or more devices, a device associated with the message segment 205-*a*-3 may be determined. In other words, in accordance with various embodiments described herein, the device (i.e., device type, device model, or device manufacturer) that originally output the message segment 205-*a*-3 (and the associated physiological measurements) may be determined from the unorganized dataset 200 by matching the format of the message segment 205-*a*-3 to a message segment format 410 that is known to be output by a particular device (e.g., device type, device model, or device manufacturer).

For example, the message segment format 405 of message segment 205-*a*-3 includes a MSI 406 followed by fourteen sequences 407. As shown, some of the sequences 407 associated with message segment 205-*a*-3 contain null values, while other sequences of sequences 407 contain information. For example, for the message segment 205-*a*-3, the MSI 406 is OBX. The following six sequences (S1 through S6) include information (measurements, parameters, etc.), while sequences 7 through 10 are null (N), as shown in 405. In addition, in this example, sequences 11 and 14 also contain information, while sequences 12 and 13 are null.

Based on the message segment format 405, a device associated with the message segment 205-*a*-3 may be determined by comparing the message segment format 405 with message segment formats 410 associated with or known to correspond with one or more devices.

Figure 4B:
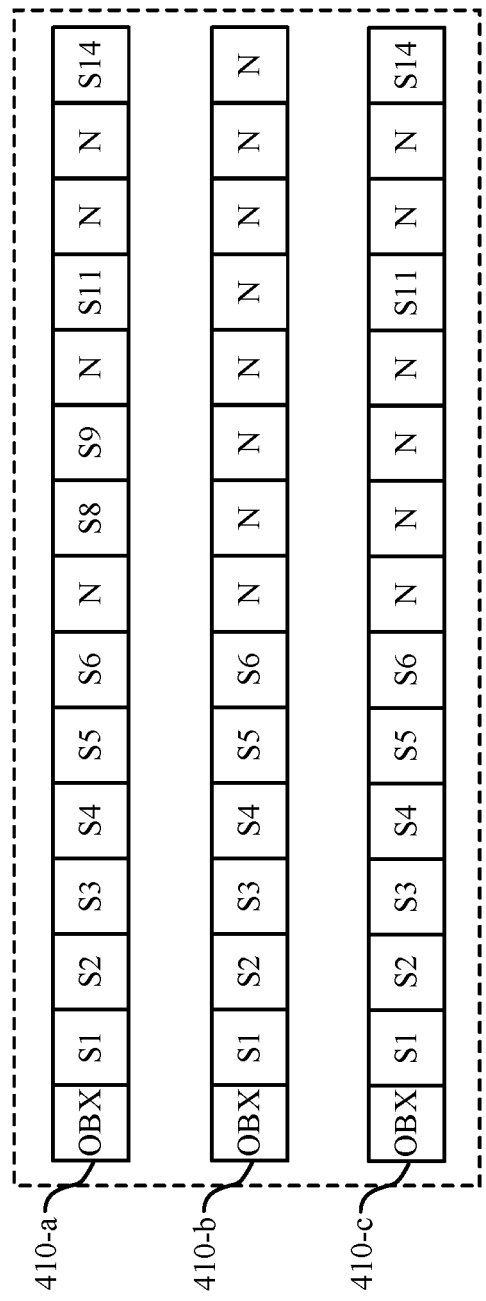

As shown in FIG. 4B, a first device may be associated with message segment format 410-*a* that includes information for sequences 1-6, 8, 9, 11, and 14, while the remaining sequences are null. A second device may be associated with message segment format 410-*b* that includes information for sequences 1-6, while the remaining sequences are null. A third device may be associated with message segment format 410-*c* that includes information for sequences 1-6, 11, and 14, while the remaining sequences are null. In this instance, as the message segment format 405 of message segment 205-*a*-3 matches the message segment format 410-*c* associated with the third device, it may be determined that the third device generated, recorded, or otherwise obtained the message segment 205-*a*. Once the device associated with the message segment 205-*a*-3 is determined, at least a portion of the dataset 200 (e.g., the measured physiological values) may be displayed in a visual format associated with the determined device.

In some embodiments, different manufacturers or models of a given device type (e.g., ventilator, heart rate sensor, capnograph) may output additional information. Therefore, a device type may be determined based on a partial match between message segment format 405 and message segment formats 410 associated with one or more devices. For example, while the message segment format 405 includes information in sequences 1-6, 11, and 14, both the first device and the third device output information in each of sequences 1-6, 11, and 14. In this instance, the first device and the third device may be ventilators (device type), and determining the difference between the first and third devices may not be as relevant and thus, at least a subset of dataset 200 may be displayed based on determining the device type, which may be a generic ventilator display.

Figure 6B:
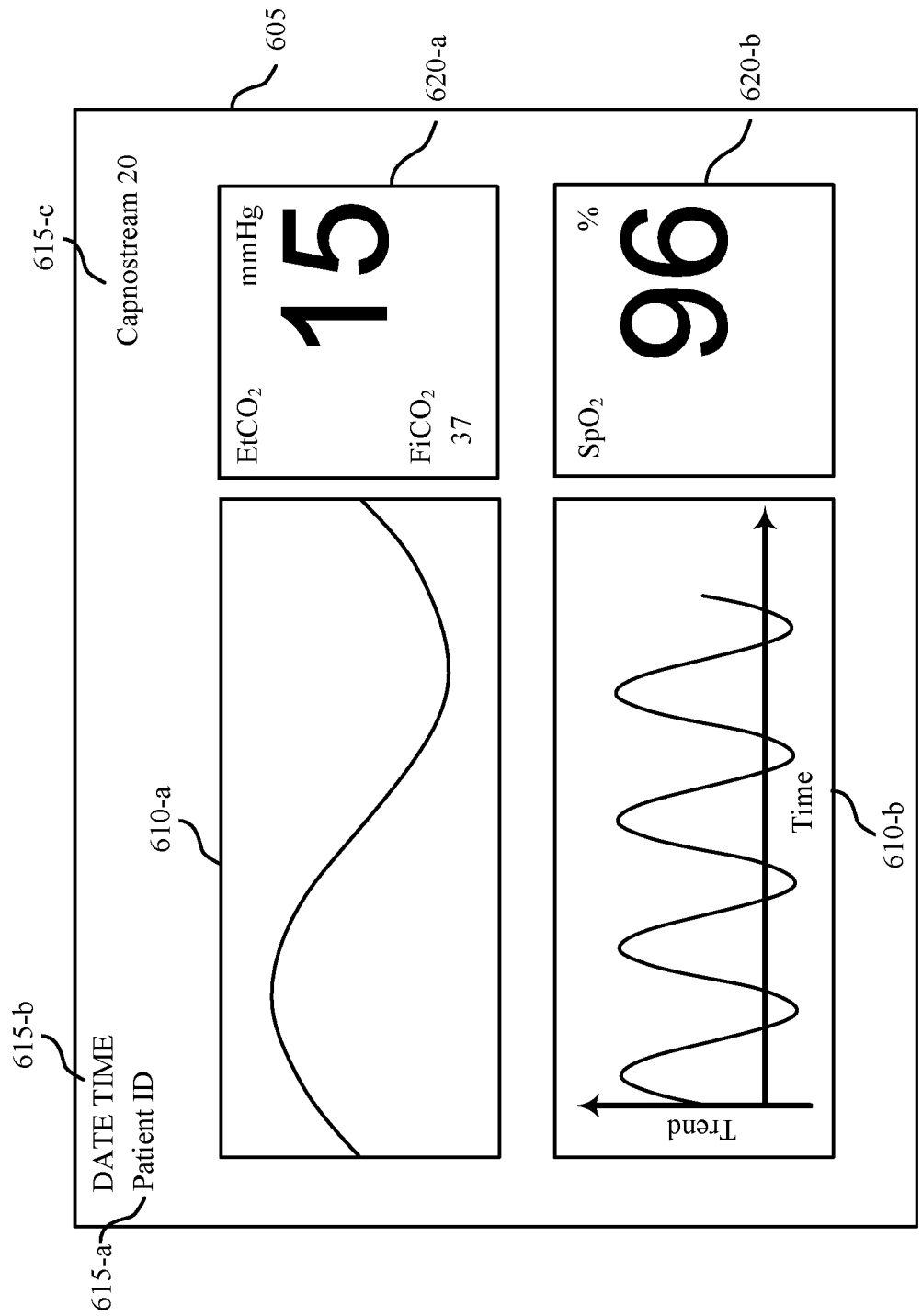
FIG. 6B shows an example displaying at least a portion of a medical dataset in accordance with aspects of the present disclosure.

In other embodiments, it may be beneficial to identify the device type as well as the device model or manufacturer. For example, the first device may correspond to a manufacturer or model different from the manufacturer or model of the third device. As such, while both the first and third device may have output message segment 205-*a*-3 (due to the partial matching between message segment format 405 with message segment formats 410-*a* and 410-*b*), as the first device 410-*a* also outputs information in sequences 8 and 9, it may be determined that the third device (which may differentiate over the first device based on device model or device manufacturer) output the message segment 205-*a*-3. Therefore, in accordance with aspects of the disclosure, at least a subset of the dataset 200 may be displayed (as shown in FIG. 6B, for example) based on the determined device type, device model, or device manufacturer.

Figure 5A:
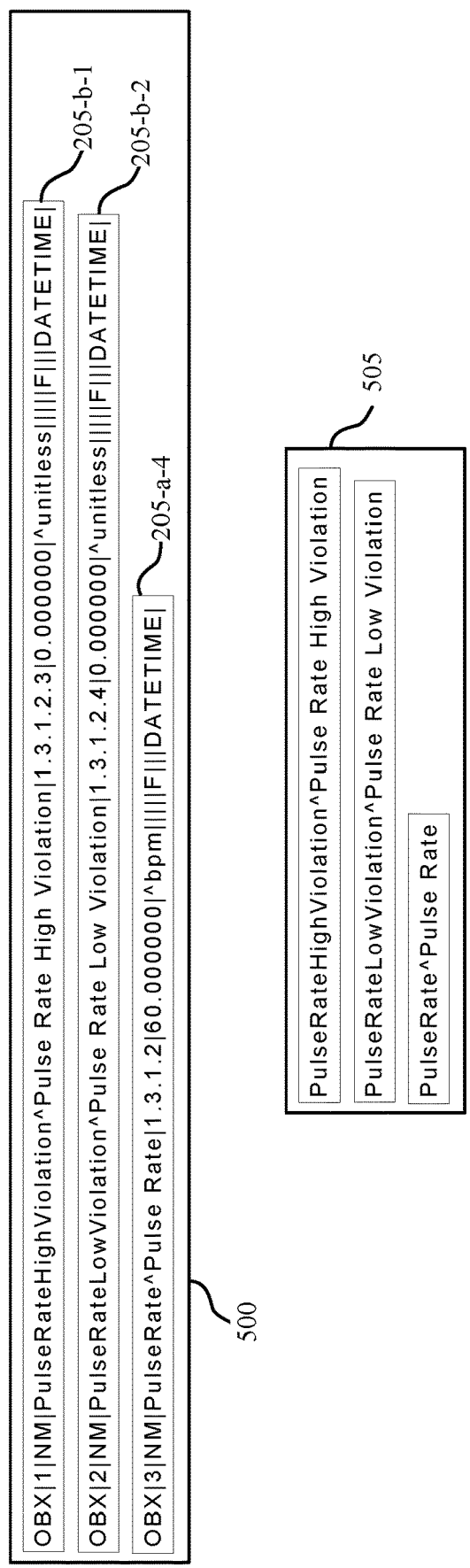
FIGS. 5A-5B illustrate examples of message segment formats in accordance with aspects of the present disclosure.

FIG. 5A shows a message segment group 500 including message segments 205-*a*-4, 205-*b*-1, and 205-*b*-2, which may be an example of aspects of dataset 200 described with reference to FIGS. 2A-2B. As shown in FIG. 5A, message segments 205-*a*-4, 205-*b*-1, and 205-*b*-2 include data (e.g., measurements, parameters, groups of parameters, etc.) associated with patient 105. Message segment 205-*a*-4 includes parameters related to a physiological measurement taken from the patient 105 as well as other parameters associated with the physiological measurement or message segment 205-*a*-4. For example, as shown in message segment 205-*a*-4, a pulse rate of 60 bpm (based on Sequences 3, 5, and 6) was measured at a given date and time (based on Sequence 14). Preceding message segment 205-*a*-4 are message segments 205-*b*-1 and 205-*b*-2, which include parameters related to pulse rate alarm limits (e.g., a PulseRateHighViolation in Sequence 3 of message segment 205-*b*-1 and PulseRateLowViolation of Sequence 3 in message segment 205-*b*-2).

As shown in 505, parameters corresponding to Sequence 3 in message segments 205-*b*-1, 205-*b*-2, and 205-*a*-4 are arranged in a particular order (i.e., PulseRateHighViolation^PulseRateHighViolation followed by PulseRateLowViolation^PulseRateLowViolation and then PulseRate^PulseRate). This parameter order may vary by device type, device model, or device manufacturer. In some embodiments, information related to the order of parameters corresponding to different sequences of different devices may be predetermined or stored in a memory of a medical device 110, computing device 115, a central station 135, or a remote computing device 145, or may be stored on various databases 140 as described with reference to FIG. 1. Therefore, by comparing the order of the parameters corresponding to Sequence 3 in message segments 205-*b*-1, 205-*b*-2, and 205-*a*-4, as shown in 505, with a known order of parameters corresponding to Sequence 3 of one or more devices, a device associated with the message segment group 500 may be determined. In other words, in accordance with various embodiments described herein, the device (i.e., device type, device model, or device manufacturer) that originally output the message segment group 500 (and the associated physiological measurements) may be determined from the unorganized dataset 200 by matching the message segment order of the message segment group 500 (e.g., the order in which the Sequence 3 parameters are listed) to a message segment order that is known to be output by a particular device (e.g., device type, device model, or device manufacturer).

Figure 5B:
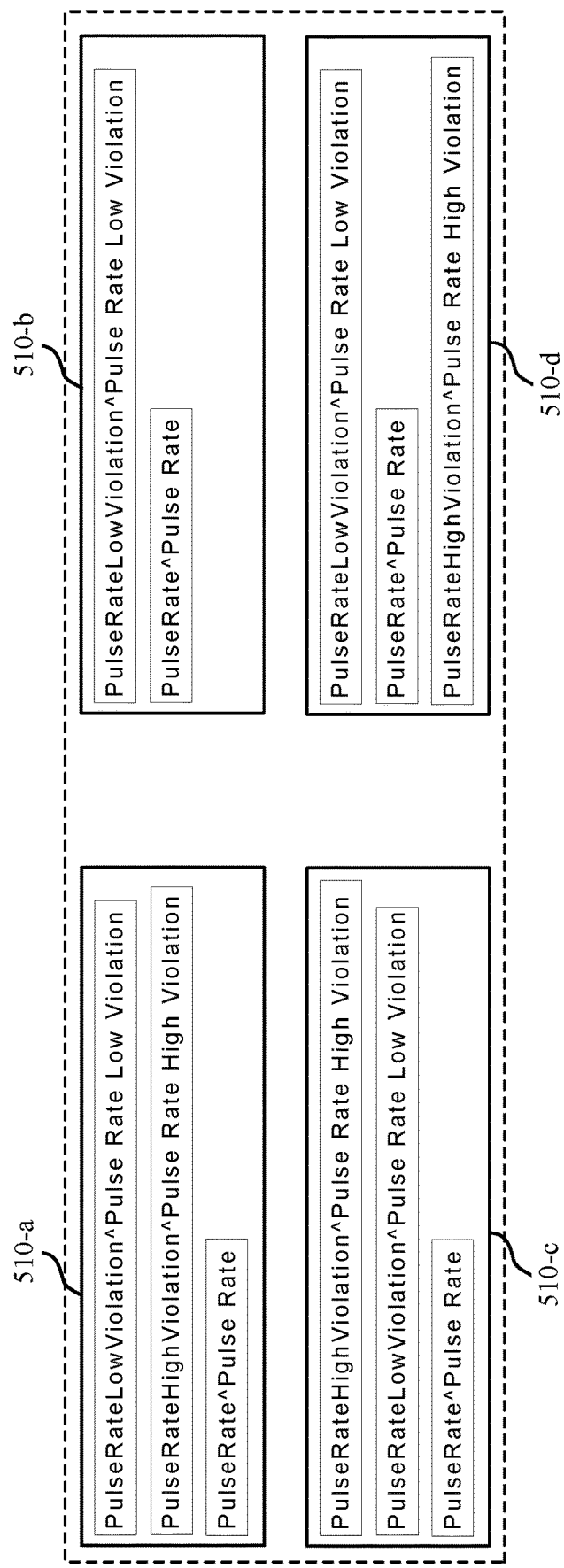

For example, as shown in FIG. 5B, a first device may generate Sequence 3 message segments in the order of PulseRateLowViolation^PulseRateLowViolation followed by PulseRateHighViolation^PulseRateHighViolation and then PulseRate^PulseRate, as represented by 510-*a*. A second device may generate Sequence 3 message segments in the order of PulseRateLowViolation^PulseRateLowViolation followed by PulseRate^PulseRate and may not generate a message segment relating to PulseRateHighViolation^PulseRateHighViolation, as represented by 510-*b*. A third device may generate Sequence 3 message segments in the order of PulseRateHighViolation^PulseRateHighViolation followed by PulseRateLowViolation^PulseRateLowViolation and then PulseRate^PulseRate, as represented by 510-*c*, while a fourth device may generate Sequence 3 message segments in the order of PulseRateLowViolation^PulseRateLowViolation followed by PulseRate^PulseRate and then PulseRateHighViolation^PulseRateHighViolation, as represented by 510-*d*.

In this instance, as the order of parameters corresponding to Sequence 3 in the third device (shown by 510-*c*) corresponds to the order of parameters associated with Sequence 3 in message segments 205-*b*-1, 205-*b*-2, and 205-*a*-4, as shown in 505 (FIG. 5A), it may be determined that the third device generated, recorded, or otherwise obtained the message segment group 500.

In the context of the above example, determining a device (e.g., the third device) associated with a particular group of message segments (e.g., message segments 500) may include determining a device type (e.g., a heart rate monitor), a device model, a device manufacturer, or a particular healthcare facility corresponding to the device.

For example, in some embodiments, one or more devices may be associated with a particular health care facility. The particular health care facility may only use certain manufacturers and models of a given device or may generate data in a format associated with that particular health care facility. As such, one or more parameters or the order of one or more parameters in message segments 500 may be compared to one or more devices or formats associated with a particular health care facility. Further, the particular health care facility may have a database of devices used at the facility. The database may contain information such as location information of a device (e.g., room number in which the device is located), serial numbers associated with the device, device type, device manufacturer, device model, or other information associated with the device. Accordingly, parameters of the one or more parameters in message segments 500 may be compared to parameters known to correspond with devices in the database of devices used at the facility and a device associated with message segment group 500 may be determined based on the comparison.

In some embodiments, device specific information (e.g., a device serial number, a room number associated with the device, etc.) may be included in one or more parameters of the message segments 500. In such instances, the device specific information may be compared with information in a predetermined database of known devices. The predetermined database of known devices may be specific to a health care facility or the types of devices contained within the predetermined database, for example, and a device type, device model, or device manufacturer associated with the message segment group 500 may be determined based on the comparison. It should be understood that while only four devices are discussed in FIGS. 5A-5B, many other devices (e.g., devices associated with a particular health care facility) and numbers of devices may be considered when determining the device type, device model, or device manufacturer associated with the message segment group 500. Once the device associated with the message segment group 500 is determined, at least a portion of the dataset 200 (e.g., the measured physiological values) may be displayed in a visual format associated with the determined device.

FIG. 6A shows an exemplary unorganized dataset 600 in accordance with various aspects of the present disclosure. In one or more embodiments, using systems or methods discussed above with respect to FIGS. 1-5, data may be obtained (e.g., physiological data recorded from a medical device 110) and the resulting dataset 600 may be stored, transmitted, or otherwise arranged in a format that is unsuitable for viewing by a clinician (e.g., for data storage or transmission reasons). However, by identifying information within the dataset 600 (measurements, parameters, or one or more groups of parameters, etc.), a medical device associated with at least a portion of the dataset 600 (e.g., the medical device that recorded the data) may be determined. Based on the determination, at least a subset of the data from the dataset 600 may be displayed (e.g., data may be displayed on a medical device 110, computing device 115, a central station 135, or a remote computing device 145 (e.g., via network 125) as described with reference to FIG. 1) in a visual format more suitable for viewing (e.g., in a visual format that corresponds to the determined device).

For example, as shown in FIG. 6B, at least a portion of dataset 600 may be displayed on a display 605. The display 605 may include one or more graphs 610, such as a streaming plot 610-*a* and a trend plot 610-*b*. The display may also include patient information 615-*a*, date and time information 615-*b*, or other information such as a device model and type 615-*c* obtained or determined from the dataset 600. In some embodiments, at least a subset of the dataset 600, such as measurements associated with a physiological parameter of a patient, may be displayed, as shown by display sections 620-*a* and 620-*b*. In this example, display section 620-*a* shows carbon dioxide concentration of 15 mmHg, while display section 620-*b* shows oxygen saturation of 96%.

Further, the visual format may be based at least in part on the determined medical device. For example, once a medical device type is determined (e.g., through any of the methods described with reference to FIGS. 3-5), other information such as a model (e.g., a manufacturer model) associated with the medical device type may be determined based on predetermined information indicative of the medical device or from other data within the dataset 600. Thus, the visual format in which at least a subset of the dataset 600 is displayed may be based on or correspond with the determined medical device type or a model of the determined medical device type (e.g., the visual format may correspond with a default format associated with the determined medical device type or model). For example, a determined model of a medical device may be a Capnostream 20, as shown by 615-*c* in FIG. 6B.

Further, the visual format may be based at least in part on a system (e.g., a medical device 110 configured to transmit data for visualization to a computing device 115, a central station 135, or a remote computing device 145, as described in FIG. 1) that includes one or more medical devices associated with the dataset 600 or patient. The visual format may also depend on a physiological system (e.g., skeletal system, muscular system, nervous system, respiratory system, cardiovascular system, reproductive system, digestive system, etc.) most relevant to a clinician at the time of viewing the dataset 600. In some embodiments, the visual format may be based a condition or disease state (e.g., if the patient recently recovered from a heart attack or has a respiratory disease such as emphysema). For example, certain parameters of the dataset may be relevant to a clinician when diagnosing the condition of a patient, while other parameters may not be as relevant for diagnosis and thus, only the relevant parameters of the dataset 600 may be displayed.

In one or more embodiments, the visual format may be based on clinician preference or may be customized based on manual input by the clinician. Such a customization may differ from a default visual format associated with the determined medical device type or model (e.g., the medical device that originally recorded the data). In some cases, the customized visual format based on clinician preference may automatically become the visual format in which data from the dataset 600 is displayed. For example, if a given clinician is often concerned with respiratory system of a patient, a visual format may be customized by the clinician to display data relevant to the respiratory system of the patient and data may automatically be displayed in the customized visual format (e.g., through machine learning algorithms that detect the reoccurring preferences of a particular clinician). In some embodiments, the visual format may correspond to a particular health care facility. For example, a particular health care facility may specialize in the cardiovascular system of a patient and data may displayed in a visual format that is suitable for viewing data of the cardiovascular system.

Figure 7:
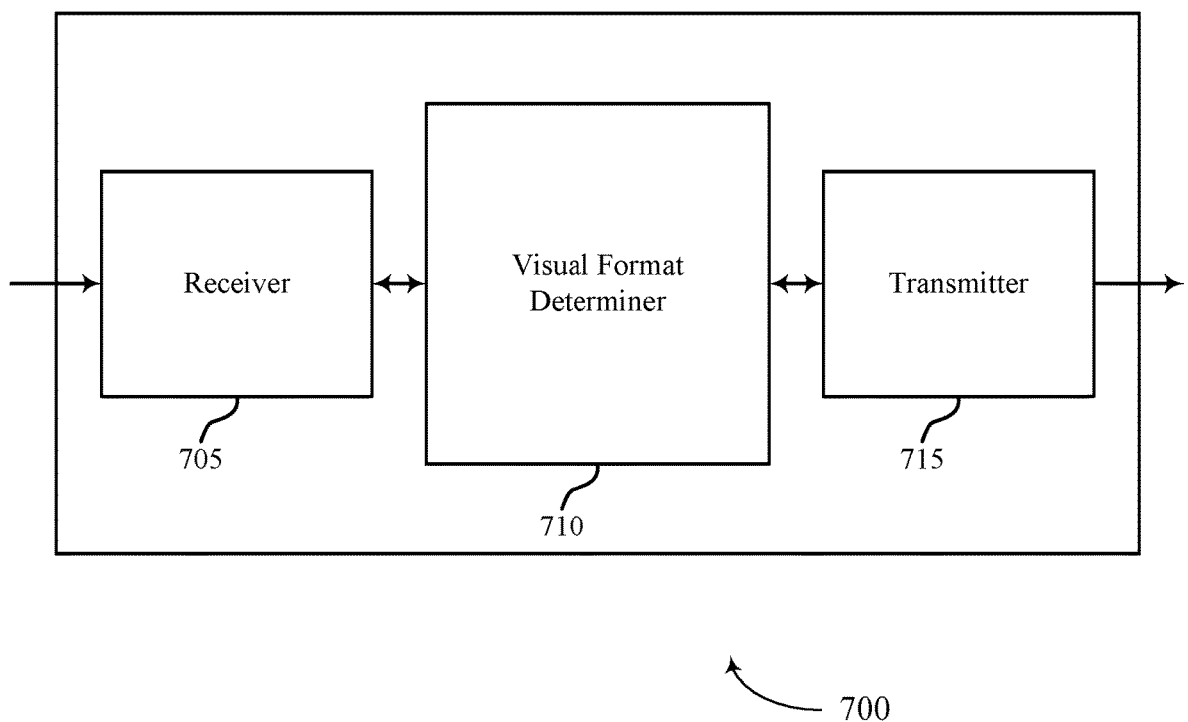
FIGS. 7-9 illustrate devices for visualizing medical data in accordance with aspects of the present disclosure.

FIG. 7 shows a block diagram of a device 700 that supports visualizing medical data in accordance with various aspects of the present disclosure. The device 700 may communicate via wired and/or wireless means and may be an example of aspects of a medical device 110, computing device 115, a central station 135, or a remote computing device 145 as described with reference to FIG. 1. Device 700 may include receiver 705, visual format determiner 710 and transmitter 715. Although not shown, device 700 may also include a processor, memory, or display unit. Each of these components may be in communication with each other. Device 700 may be operable to receive and store medical data (e.g., patient data, health care facility data, measurements, parameters, etc.) and display at least a portion of the medical data in a visual format. The visual format may be based at least in part on a determined medical device associated with at least a portion of the medical data.

The receiver 705 may receive information such as packets, medical data, or control information associated with various medical devices (e.g., a pulse oximetry (SpO2) sensor, a heart rate sensor, a blood pressure sensor, a pressure sensor, an electrocardiogram (ECG) sensor, a respiratory rate sensor, a glucose level sensor, a body temperature sensor, an accelerometer, a global positioning sensor, a sensor which triangulates position from multiple computing devices 115, or any other sensor configured to collect physiological, location, or motion data). For example, the receiver 705 may receive medical data including measurements of a physiological parameter associated with a patient from a medical device of the patient such as described with reference to FIG. 1.

The receiver 705 may also receive other data such as patient information, health care facility data, clinician information, or other information which may be observed or recorded by a clinician responsible for the patient. The receiver 705 may receive data via wireless or wired means (e.g., the device 700 may receive medical data wirelessly). The receiver 705 may pass data and information on to other components (e.g., to the visual format determiner 710) of the device 700. The receiver 705 may be an example of aspects of the transceiver 920 described with reference to FIG. 9.

The visual format determiner 710 may include circuitry, logic, hardware and/or software for collecting and processing medical data received from medical devices, health care facilities, or recorded by a clinician. The medical data may be an HL7 dataset (e.g., dataset 600) and may include a plurality of physiological measurements taken from a patient and a plurality of parameters associated with the plurality of physiological measurements. The visual format determiner 710 may identify and compare one or more groups of parameters from the plurality of parameters within the HL7 dataset to determine a medical device type from which at least a portion of a plurality of physiological measurements were measured, as described with reference to FIGS. 3-5. The determination may be based at least in part on the one or more identified groups of parameters. The visual format determiner 710 may be an example of aspects of the visual format determiner 710-a and 710-b described with reference to FIGS. 8 and 9.

The transmitter 715 may transmit signals received from other components of the device 700. In some examples, the transmitter 715 may be collocated with a receiver in a transceiver module. For example, the transmitter 715 may be an example of aspects of the transceiver 925 described with reference to FIG. 9. The transmitter 715 may include a single antenna, or it may include multiple antennas. In some cases, the transmitter 715 may transmit a visual format in which to display data from the medical data. The visual format may transmitted to a display of a medical device 110, computing device 115, a central station 135, or a remote computing device 145, as described with reference to FIG. 1. In other cases, the device 700 may include a display and may display at least a subset of the data in a visual format determined by the visual format determiner 710.

Figure 8:
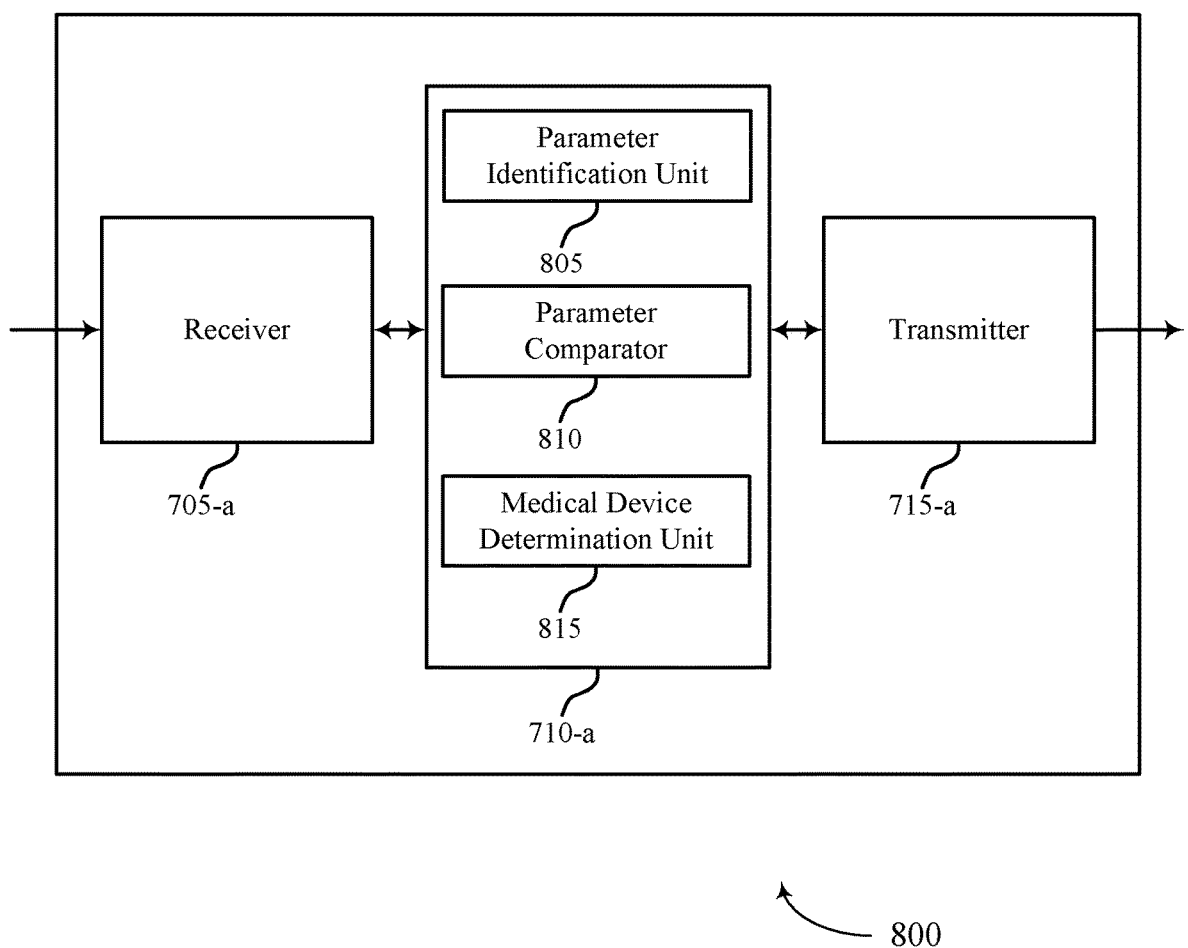

FIG. 8 shows a block diagram of a device 800 that supports visualizing medical data in accordance with various aspects of the present disclosure. The device 800 may be an example of aspects of a medical device 110, computing device 115, a central station 135, a remote computing device 145, or a device 700 described with reference to FIGS. 1 and 7. The device 800 may include receiver 705-a, visual format determiner 710-a, and transmitter 715-a. Although not shown, the device 800 may also include a processor, memory, and a display unit. Each of these components may be in communication with each other. The device 800 may communicate via wired and/or wireless means.

The receiver 705-a may receive such as packets, medical data, or control information associated with various medical devices (e.g., a pulse oximetry (SpO2) sensor, a heart rate sensor, a blood pressure sensor, a pressure sensor, an electrocardiogram (ECG) sensor, a respiratory rate sensor, a glucose level sensor, a body temperature sensor, an accelerometer, a global positioning sensor, a sensor which triangulates position from multiple computing devices 115, or any other sensor configured to collect physiological, location, or motion data) which may be passed on to other components of the device 800. The receiver 705-a may also perform the functions described with reference to the receiver 705 of FIG. 7. The transmitter 715-a may transmit signals received from other components of the device 800. In some examples, the transmitter 715-a may be collocated with a receiver in a transceiver module. For example, the receive 705-a and transmitter 715-a may be an example of aspects of the transceiver 920 described with reference to FIG. 9. The transmitter 715-a may utilize a single antenna, or may utilize a plurality of antennas.

The visual format determiner 710-a may be an example of aspects of visual format determiner 710 described with reference to FIG. 7. The visual format determiner 710-a may include a parameter identification unit 805, a parameter comparator 810, and a medical device determination unit 815. The visual format determiner 710-a may be an example of aspects of the visual format determiner 710-b described with reference to FIG. 9. The visual format determiner 710-a may receive, via receiver 705-a, medical data including measurements of a physiological parameter associated with a patient from a medical device of the patient such as described with reference to FIG. 1. The visual format determiner 710-a may also receive, via receiver 705-a other data such as patient information, health care facility data, clinician information, or other information which may be observed or recorded by a clinician responsible for the patient.

The parameter identification unit 805 may include circuitry, logic, hardware and/or software for identifying parameters (measurements, patient information, health care facility information, clinician information, etc.) of within an unorganized medical dataset (e.g., dataset 600). In some cases, the parameter identification unit 805 may identify one or more groups of parameters associated with a patient or a plurality of physiological measurements taken from the patient. In some embodiments, the parameter identification unit 805 may identify the format of the medical data. For example, the parameter identification unit 805 may identify that the medical data is arranged in an HL7 standard format. In other embodiments, the parameter identification unit 805 may identify that the medical data is arranged in other formats. Identifying the format may include determining the format in which the medical data is arranged by comparing the arrangement of medical data to known standard formats or other formats associated with a medical device, a healthcare facility, or a clinician, as described with reference to FIGS. 4A-4B.

The parameter comparator 810 may include circuitry, logic, hardware and/or software for comparing the one or more groups of parameters identified by the parameter identification unit 805 with one or more predetermined groups of parameters indicative of a medical device type. In some embodiments, the parameter comparator 810 may compare the identified one or more groups of parameters with one or more predetermined groups of parameters indicative of the determined model of a medical device type, as described with reference to FIGS. 3A-3B. The parameter comparator 810 may compare the identified one or more groups of parameters with one or more predetermined groups of parameters indicative of a manufacturer of the medical device type. In some embodiments, the parameter comparator 810 may compare the identified one or more groups of parameters with one or more predetermined groups of parameters indicative of a healthcare facility.

The medical device determination unit 815 may include circuitry, logic, hardware and/or software for determining a medical device type associated with a medical dataset, as described with reference to FIGS. 3-5. In some embodiments, the medical device determination unit 815 may determine at least a medical device type from which at least a portion of a plurality of the physiological measurements were measured. The determination may be based at least in part on the one or more identified groups of parameters or may be based on the comparison performed by the parameter comparator 810. In some embodiments, the medical device determination unit 815 may determine a medical device model or manufacturer associated with a medical device type. In other embodiments, the medical device determination unit 815 may determine a healthcare facility from which one or more physiological measurements were measured. Based on the determination, a visual format in which at least a subset of the data may be displayed.

Figure 9:
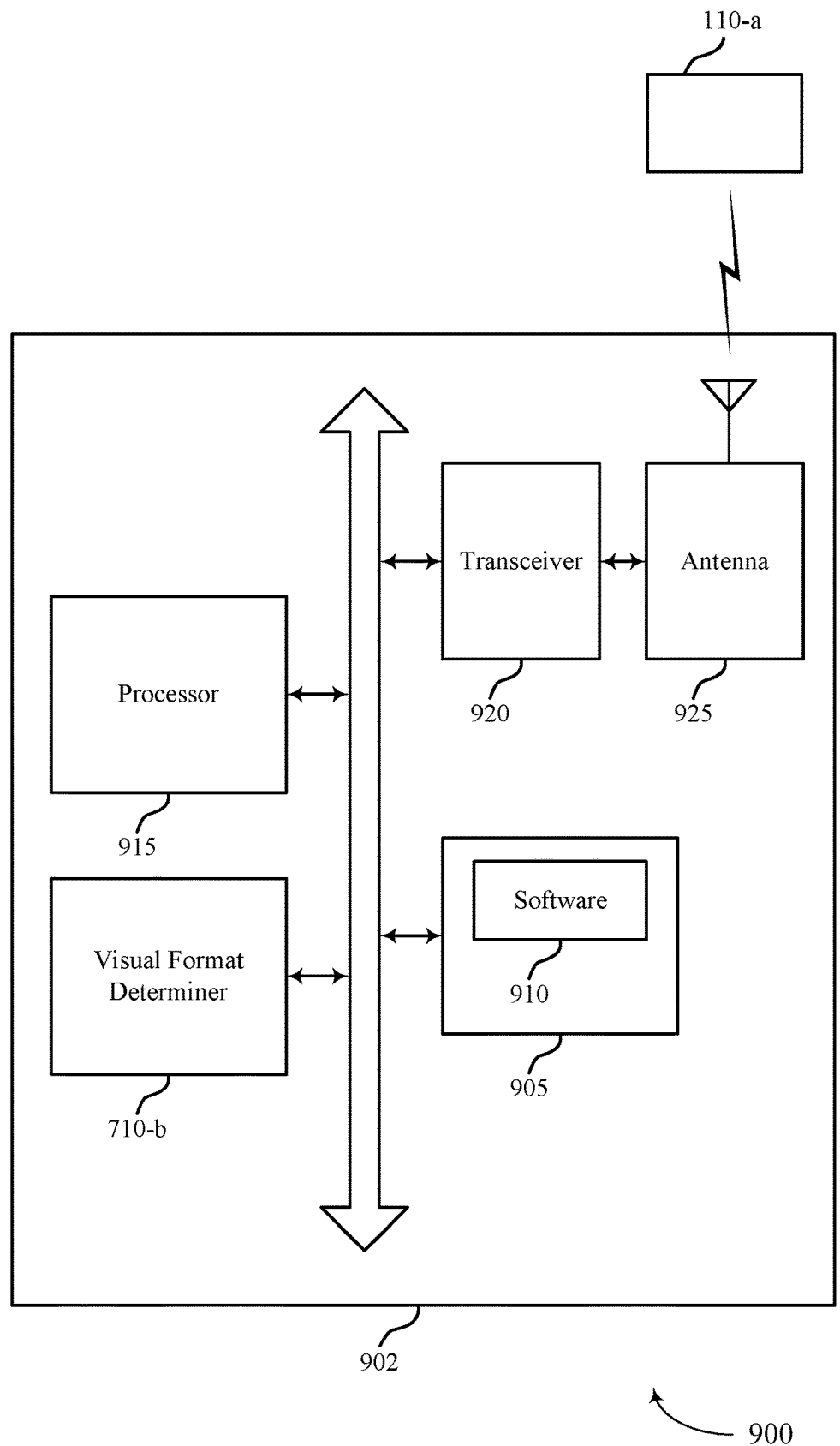

FIG. 9 shows a diagram of a system 900 that supports visualizing medical data in accordance with various aspects of the present disclosure. System 900 may include a device 902, which may be an example of a medical device 110, a computing device 115, a central station 135, a remote computing device 145, or a device 700 or 800 described with reference to FIGS. 1, 7, and 8. System 900 may also include a sensor 110-a, which may be an example of a medical device 110 described with reference to FIGS. 1, 7, and 8. Sensor 110-a may be configured to receive, obtain, collect, process, or store medical data received from medical devices, health care facilities, or recorded by a clinician associated with a patient. The medical data may be an HL7 dataset (e.g., dataset 600) and may include a plurality of physiological measurements taken from a patient and a plurality of parameters associated with the plurality of physiological measurements. Device 902 may be configured to identify and compare one or more groups of parameters from the plurality of parameters within the HL7 dataset to determine a medical device type from which at least a portion of a plurality of physiological measurements were measured. The determination may be based at least in part on the one or more identified groups of parameters.

Device 902 may include visual format determiner 710-b, which may be an example of a visual format determiner 710 described with reference to FIGS. 7 and 8. Device 902 may also include memory 905, processor 915, transceiver 920, and antenna 925. Each of these modules may communicate, directly or indirectly, with one another (e.g., via one or more buses). The memory 905 may be in electronic communication with the processor 915 and may include random access memory (RAM) and read only memory (ROM). The memory 905 may store computer-readable, computer-executable software (e.g., software 910) including instructions that, when executed, cause the processor to perform various functions described herein (e.g., determine a medical device associated with an unorganized data set and visualize the medical data accordingly). In some cases, the software 910 may not be directly executable by the processor but may cause a computer (e.g., when compiled and executed) to perform functions described herein.

The processor 915 may include an intelligent hardware device, (e.g., a central processing unit (CPU), a microcontroller, an application specific integrated circuit (ASIC), etc.). The transceiver 920 may communicate bi-directionally, via one or more antennas, wired, or wireless links, with one or more networks, as described above. The transceiver 920 may also include a modem to modulate the packets and provide the modulated packets to the antennas for transmission, and to demodulate packets received from the antennas. In some cases, device 902 may include a single antenna 925. However, in some cases the device may have more than one antenna 925, which may be capable of concurrently transmitting or receiving multiple wireless transmissions.

Figure 10:
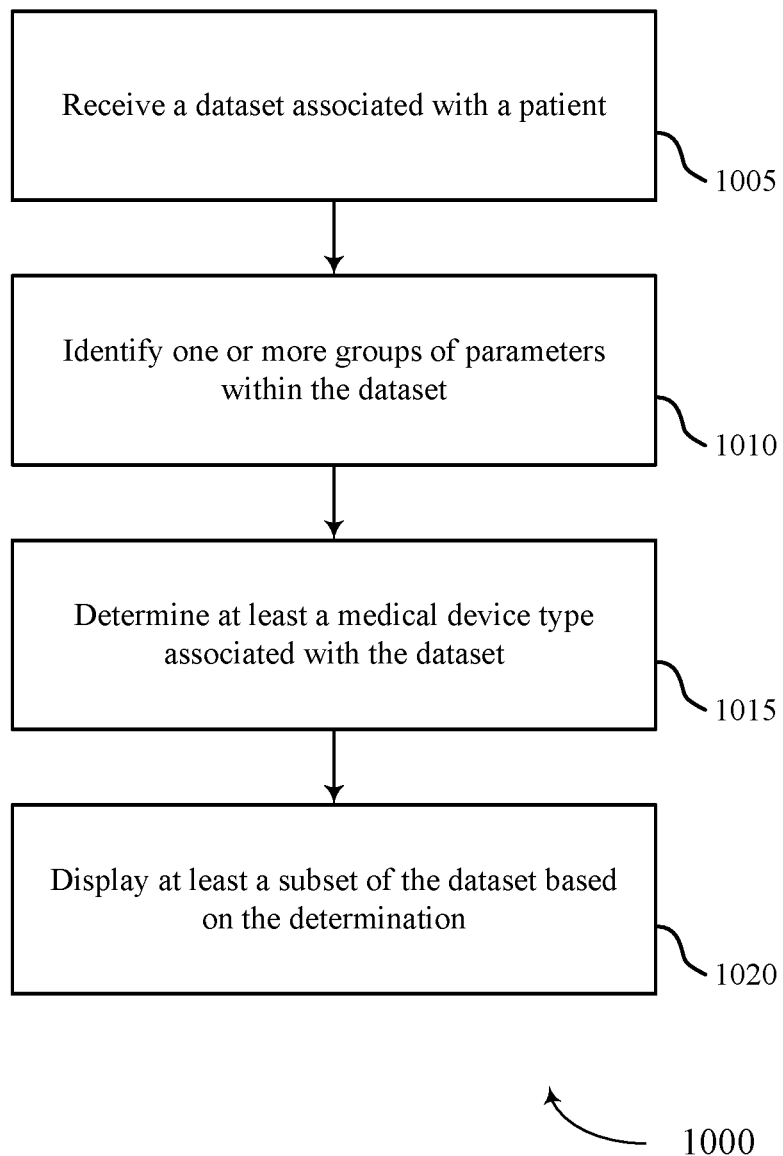
FIG. 10 illustrates a method for visualizing medical data in accordance with aspects of the present disclosure.

FIG. 10 shows a flowchart illustrating a method 1000 for visualizing medical data in accordance with various aspects of the present disclosure. The operations of method 1000 may be implemented by a device such as a medical device 110, computing device 115, a central station 135, a remote computing device 145, or device 700, device 800, device 902, or its components as described with reference to FIGS. 1 and 7-9. For example, the operations of method 1000 may be performed by the visual format determiner 710 as described herein. In some examples, device may execute a set of codes to control the functional elements of the device to perform the functions described below. Additionally or alternatively, the device may perform aspects the functions described below using special-purpose hardware.

At block 1005, the method may include receiving a dataset (e.g., dataset 600) associated with a patient as described above with reference to FIGS. 1 and 7-9. In certain examples, the operations of block 1005 may be performed by the receiver 705 as described with reference to FIGS. 7-9.

At block 1010, the method may include identifying one or more groups of parameters within the received dataset as described above with reference to FIGS. 2-9. In certain examples, the operations of block 1010 may be performed by the visual format determiner 710 as described with reference to FIGS. 7-9.

At block 1015, the method may include determining at least a medical device type associated with the dataset as described above with reference to FIGS. 2-9. In some cases, determining the medical device type includes comparing one or more groups of parameters with one or more predetermined groups of parameters indicative of the determined manufacturer, model, or type associated with a medical device. Determining the medical device type may include determining at least a medical device type from which at least a portion of a plurality of the physiological measurements were measured. The determination may be based at least in part on the one or more identified groups of parameters or may be based on the comparison. In some embodiments, determining may involve determining a healthcare facility from which one or more physiological measurements were measured.

At block 1020, the method may include displaying at least a subset of the dataset based on the determining at block 1015. The displaying may be based at least in part on the determined medical device type, model, manufacturer, health care facility, or clinician preference as described above with reference to FIGS. 6A and 6B. For example, displaying may involve displaying at least a subset of the dataset in a visual format corresponding to a default visual format of a determined manufacturer, type, or model associated with a medical device. In some cases, displaying includes displaying at least the subset of the plurality of physiological measurements from the dataset in a visual format, the visual format based at least in part on the determined medical device type, a physiological system associated with at least one of the plurality of physiological measurements, or a condition of the patient. In other embodiments, displaying may include displaying at least the subset of the plurality of physiological measurements from the HL7 dataset in a visual format that corresponds to a predetermined visual format associated with a determined healthcare facility. The displaying may be customized based at least in part on manual inputs by a clinician and the customized visual format may differ from a default visual format of a determined medical device.

It should be noted that these methods describe possible implementations, and that the operations and the steps may be rearranged or otherwise modified such that other implementations are possible. In some examples, aspects from two or more of the methods may be combined. For example, aspects of each of the methods may include steps or aspects of the other methods, or other steps or techniques described herein. Thus, aspects of the disclosure may provide for visualizing medical data.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed herein.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more") indicates an inclusive list such that, for example, a list of at least one of A, B, or C means A or B or C or AB or AC or BC or ABC (i.e., A and B and C).

Thus, aspects of the disclosure may provide for visualizing medical data. It should be noted that these methods describe possible implementations, and that the operations and the steps may be rearranged or otherwise modified such that other implementations are possible. In some examples, aspects from two or more of the methods may be combined.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

What is claimed is:

1. A method for visualizing medical data, the method comprising:

receiving, from a medical device, a medical dataset associated with a patient, the medical dataset comprising a plurality of message segments that comprises a plurality of physiological measurements taken from the patient and a plurality of parameters associated with the plurality of physiological measurements, each of the plurality of parameters separated from each of the plurality of physiological measurements by a separator;

identifying, by a processor, an order of one or more groups of parameters and physiological measurements from the medical dataset, wherein the order of the one or more groups is indicative of an arrangement within the medical dataset;

comparing, by the processor, the order of the one or more groups with a predetermined order of one or more groups of parameters and physiological measurements based at least in part on identifying the order of the one or more groups, wherein the predetermined order of the one or more groups is indicative of a medical device type;

identifying, by the processor, at least a match between the order of the one or more groups and the predetermined order of the one or more groups based at least in part on the comparing;

determining, by the processor, at least the medical device type from which at least a portion of the plurality of physiological measurements were measured in response to identifying at least the match between the order of the one or more groups and the predetermined order of the one or more groups;

determining a model of the medical device type or a manufacturer of the medical device type based at least in part on determining the medical device type, wherein determining the model of the medical device type or the manufacturer of the medical device type comprises comparing the order of the one or more groups with one or more predetermined groups of parameters indicative of the model of the medical device type or the manufacturer of the medical device type; and displaying an arrangement of at least a subset of the plurality of physiological measurements from the medical dataset, wherein the arrangement corresponds to a default arrangement displayed on the medical device type, wherein the displaying is based at least in part on determining the medical device type, the model of the medical device type, or the manufacturer of the medial device type.

2. The method of claim 1, wherein the displaying comprises displaying at least the subset of the plurality of physiological measurements from the medical dataset in a visual format, the visual format based at least in part on the determined medical device type, a physiological system associated with at least one of the plurality of physiological measurements, or a condition of the patient.

3. The method of claim 1, wherein the displaying comprises displaying at least the subset of the plurality of physiological measurements from the medical dataset in a visual format, the visual format corresponding to a default visual format of the determined medical device type.

4. The method of claim 1, wherein the displaying comprises displaying at least the subset of the plurality of physiological measurements from the medical dataset in a visual format, the visual format corresponding to a default visual format of the determined model of the determined medical device type.

5. The method of claim 1, wherein the medical dataset comprises a Health Level 7 (HL7) dataset, a Fast Healthcare Interoperability Resources (FHIR) dataset, a Clinical Document Architecture (CDA) dataset, or a Consolidated CDA (C-CDA) dataset.

6. The method of claim 1, wherein the displaying comprises displaying at least the subset of the plurality of physiological measurements from the medical dataset in a visual format, the visual format customizable based at least in part on manual inputs by a clinician and the visual format differs from a default visual format of the determined medical device type.

7. The method of claim 6, wherein the displaying further comprises automatically displaying the visual format.

8. The method of claim 1, wherein the plurality of parameters comprises a unit of measurement corresponding to at least one of the plurality of physiological measurements, patient identification information, clinician identification information, or healthcare facility identification information.

9. A system for visualizing medical data, the system comprising:
a memory;
a processor in electronic communication with the memory; and
instructions stored in the memory and operable, when executed by the processor, to cause the system to:
receive, from a medical device, a medical dataset associated with a patient, the medical dataset comprising a plurality of message segments that comprises a plurality of physiological measurements taken from the patient and a plurality of parameters associated with the plurality of physiological measurements, each of the plurality of parameters separated from each of the plurality of physiological measurements by a separator;
identify, by the processor, an order of one or more groups of parameters and physiological measurements from the medical dataset, wherein the order of the one or more groups is indicative of an arrangement within the medical dataset;
compare, by the processor, the order of the one or more groups with a predetermined order of one or more groups of parameters and physiological measurements based at least in part on identifying the order of the one or more groups, wherein the predetermined order of the one or more groups is indicative of a medical device type;
identify, by the processor, at least a match between the order of the one or more groups and the predetermined order of the one or more groups based at least in part on the comparing;
determine, by the processor, at least the medical device type from which at least a portion of the plurality of physiological measurements were measured in response to identifying at least the match between the order of the one or more groups and the predetermined order of the one or more groups;
determine a model of the medical device type or a manufacturer of the medical device type based at least in part on determining the medical device type, wherein determining the model of the medical device type or the manufacturer of the medical device type comprises comparing the order of the one or more groups with one or more predetermined groups of parameters indicative of the model of the medical device type or the manufacturer of the medical device type; and
displaying an arrangement of at least a subset of the plurality of physiological measurements from the medical dataset, wherein the arrangement corresponds to a default arrangement displayed on the medical device type, wherein the displaying is based at least in part on determining the medical device type, the mode 1 of the medical device type, or the manufacturer of the medial device type.

10. The system of claim 9, wherein the instructions are operable to cause the processor to display at least the subset of the plurality of physiological measurements from the medical dataset in a visual format, the visual format based at least in part on the determined medical device type, a physiological system associated with at least one of the plurality of physiological measurements, or a condition of the patient.

11. The system of claim 9, wherein the instructions are operable to cause the processor to display at least the subset of the plurality of physiological measurements from the medical dataset in a visual format that corresponds to a default visual format of the determined medical device type.

12. The system of claim 9, wherein the instructions are operable to cause the processor to display at least the subset of the plurality of physiological measurements from the medical dataset in a visual format that corresponds to a default visual format of the determined model of the determined medical device type.

13. The system of claim 9, wherein the instructions are operable to cause the processor to display at least the subset of the plurality of physiological measurements from the medical dataset in a visual format that corresponds to a default visual format of the determined manufacturer of the determined medical device type.

14. The system of claim 9, wherein the instructions are operable to cause the processor to automatically display a customized visual format, wherein the customized visual format is based at least in part on manual inputs by a clinician and differs from a default visual format of the determined medical device type.

* * * * *